United States Patent
Gregory

(10) Patent No.: US 10,967,143 B1
(45) Date of Patent: Apr. 6, 2021

(54) MUCUS-REMOVING DEVICE

(71) Applicant: Dorethia Gregory, Temecula, CA (US)

(72) Inventor: Dorethia Gregory, Temecula, CA (US)

( * ) Notice: Subject to any disclaimer, the term of this patent is extended or adjusted under 35 U.S.C. 154(b) by 406 days.

(21) Appl. No.: 16/018,265

(22) Filed: Jun. 26, 2018

(51) Int. Cl.
*A61M 16/04* (2006.01)
*A61B 17/24* (2006.01)
*A61M 16/00* (2006.01)

(52) U.S. Cl.
CPC .... *A61M 16/0463* (2013.01); *A61M 16/0484* (2014.02); *A61B 2017/246* (2013.01); *A61M 16/047* (2013.01); *A61M 2016/0027* (2013.01); *A61M 2210/0618* (2013.01); *A61M 2210/0625* (2013.01)

(58) Field of Classification Search
CPC ........ A61M 16/0463; A61M 2017/246; A61M 2016/047; A61M 16/0484; A61M 2210/0618; A61M 2210/0625; A61M 2016/0027; A61M 16/04; A61M 16/0465; A61M 16/0468; A61M 2210/1032; A61B 1/267; A61B 17/24; A61B 2017/242; A61B 5/285
See application file for complete search history.

(56) References Cited

U.S. PATENT DOCUMENTS

| | | | |
|---|---|---|---|
| 4,366,821 A * | 1/1983 | Wittmaier | A61B 5/113 340/573.1 |
| 4,995,386 A | 2/1991 | Ng | |
| D411,616 S | 6/1999 | Retallick, II | |
| 6,227,197 B1 | 5/2001 | Fitzgerald | |
| 6,575,944 B1 | 6/2003 | McNary | |
| 7,503,328 B2 | 3/2009 | Kolobow | |
| 9,022,036 B2 * | 5/2015 | Graham | A61M 16/0465 128/207.14 |
| 2003/0212412 A1 | 11/2003 | Dillard | |
| 2004/0221851 A1 * | 11/2004 | Madsen | A61M 16/0463 128/207.14 |
| 2008/0023005 A1 * | 1/2008 | Tokunaga | A61M 16/0463 128/205.19 |
| 2012/0199127 A1 * | 8/2012 | Garde | A61M 16/024 128/204.23 |

(Continued)

FOREIGN PATENT DOCUMENTS

WO  2006099434  9/2006

*Primary Examiner* — Adam Marcetich
(74) *Attorney, Agent, or Firm* — Kyle A. Fletcher, Esq.

(57) ABSTRACT

The mucus-removing device is adapted for use with a patient. The patient is further defined with a tracheostomy tube. The mucus-removing device is configured for use with the tracheostomy tube. The mucus-removing device generates a vacuum at the tracheostomy tube such that mucus is withdrawn from the pulmonary system through the tracheostomy tube and into the mucus-removing device. The mucus-removing device generates the vacuum at the tracheostomy for a fixed period of time. The periodic nature of the generation of the vacuum allows the patient to breath comfortably during the removal process. The mucus-removing device comprises a pump, a hose, a tracheostomy tube connector, and a control system. The hose attaches the pump to the tracheostomy tube connector. The tracheostomy tube connector attaches the mucus-removing device to the tracheostomy tube of the patient. The control system regulates the operation of the pump.

17 Claims, 4 Drawing Sheets

(56) References Cited

U.S. PATENT DOCUMENTS

2014/0014103 A1* 1/2014 Smaldone ......... A61M 16/0463
                                                    128/203.12
2017/0021120 A1* 1/2017 Ash .................. A61M 16/0465
2017/0319804 A1* 11/2017 Elia .................. A61M 16/0402

* cited by examiner

MUCUS-REMOVING DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary devices including devices for removing medial from the body, more specifically, a container for suction drainage with a self-contained vacuum aspirator.

SUMMARY OF INVENTION

The mucus-removing device is adapted for use with a patient. The patient is further defined with a tracheostomy tube. The mucus-removing device is configured for use with the tracheostomy tube. The mucus-removing device generates a vacuum at the tracheostomy tube such that mucus is withdrawn from the pulmonary system through the tracheostomy tube and into the mucus-removing device. The mucus-removing device generates the vacuum at the tracheostomy for a fixed period of time. The periodic nature of the generation of the vacuum allows the patient to breath comfortably during the removal process. The mucus-removing device comprises a pump, a hose, a tracheostomy tube connector, and a control system. The hose attaches the pump to the tracheostomy tube connector. The tracheostomy tube connector attaches the mucus-removing device to the tracheostomy tube of the patient. The control system regulates the operation of the pump.

These together with additional objects, features and advantages of the mucus-removing device will be readily apparent to those of ordinary skill in the art upon reading the following detailed description of the presently preferred, but nonetheless illustrative, embodiments when taken in conjunction with the accompanying drawings.

In this respect, before explaining the current embodiments of the mucus-removing device in detail, it is to be understood that the mucus-removing device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the mucus-removing device.

It is therefore important that the claims be regarded as including such equivalent construction insofar as they do not depart from the spirit and scope of the mucus-removing device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
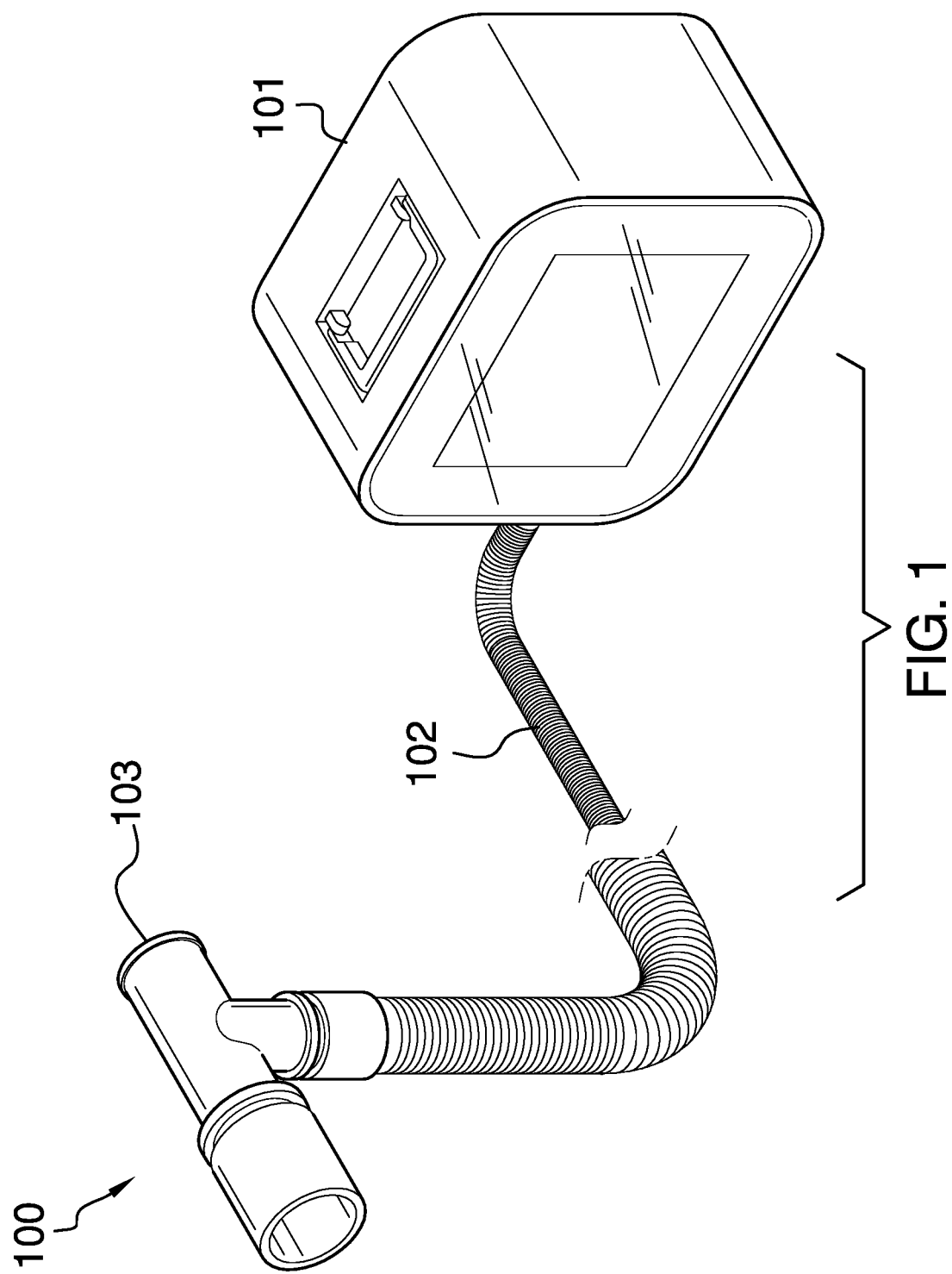
FIG. 1 is a perspective view of an embodiment of the disclosure.
Figure 2:
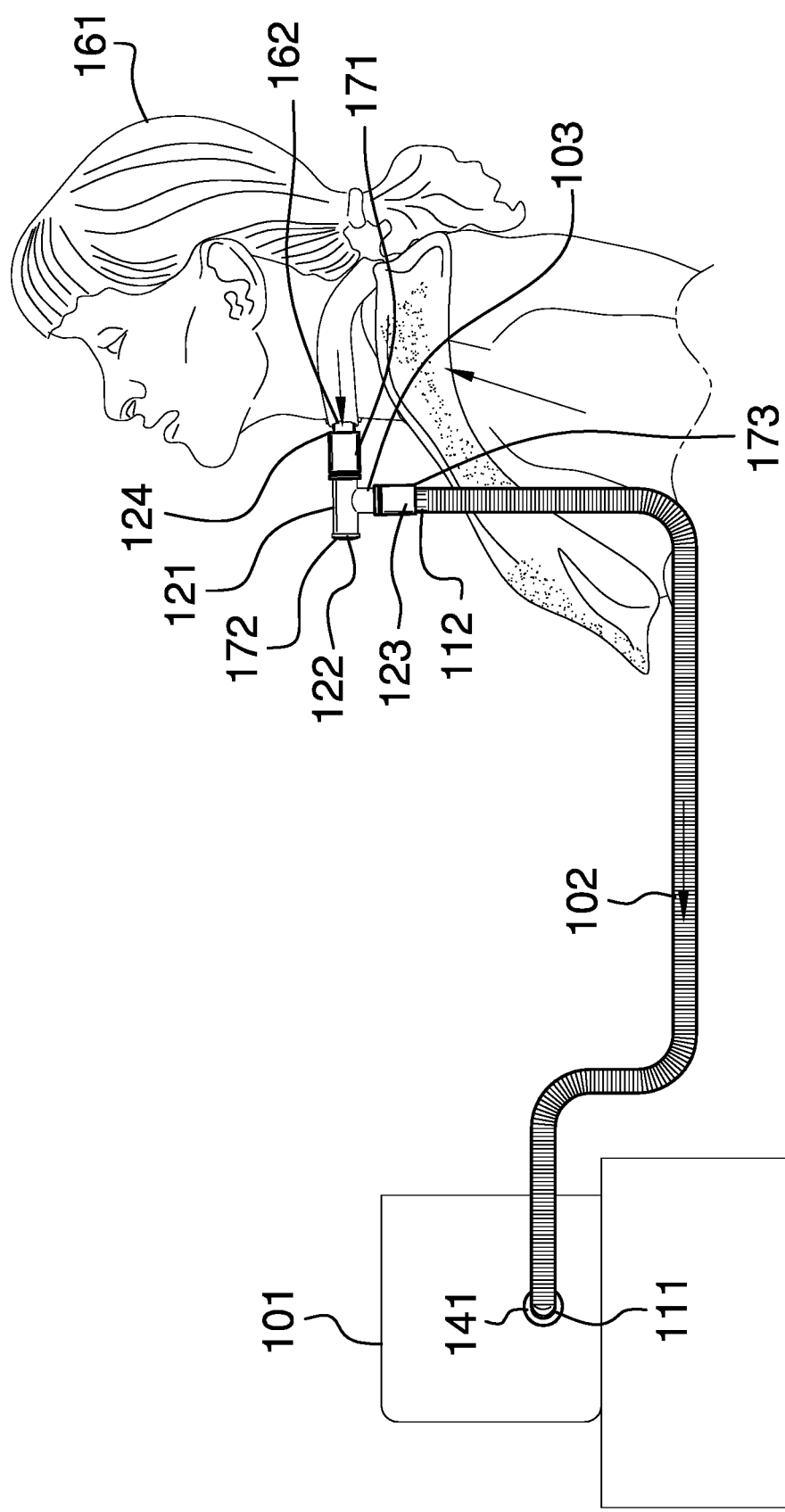
FIG. 2 is an in-use view of an embodiment of the disclosure.
Figure 3:
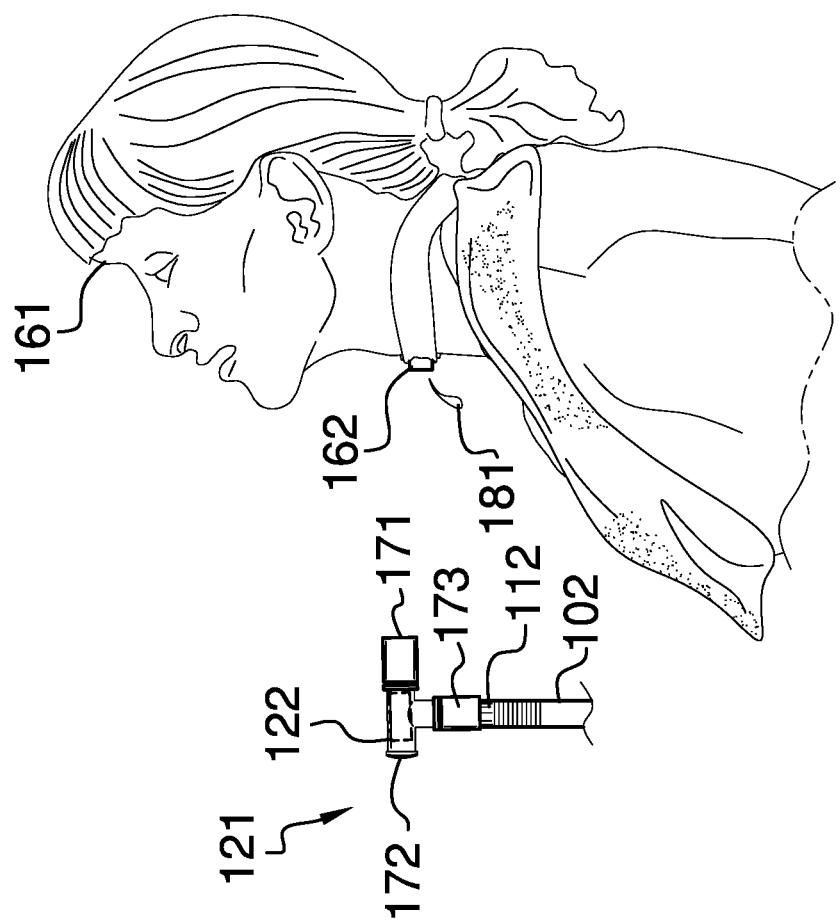
FIG. 3 is an in-use view of an embodiment of the disclosure.
Figure 4:
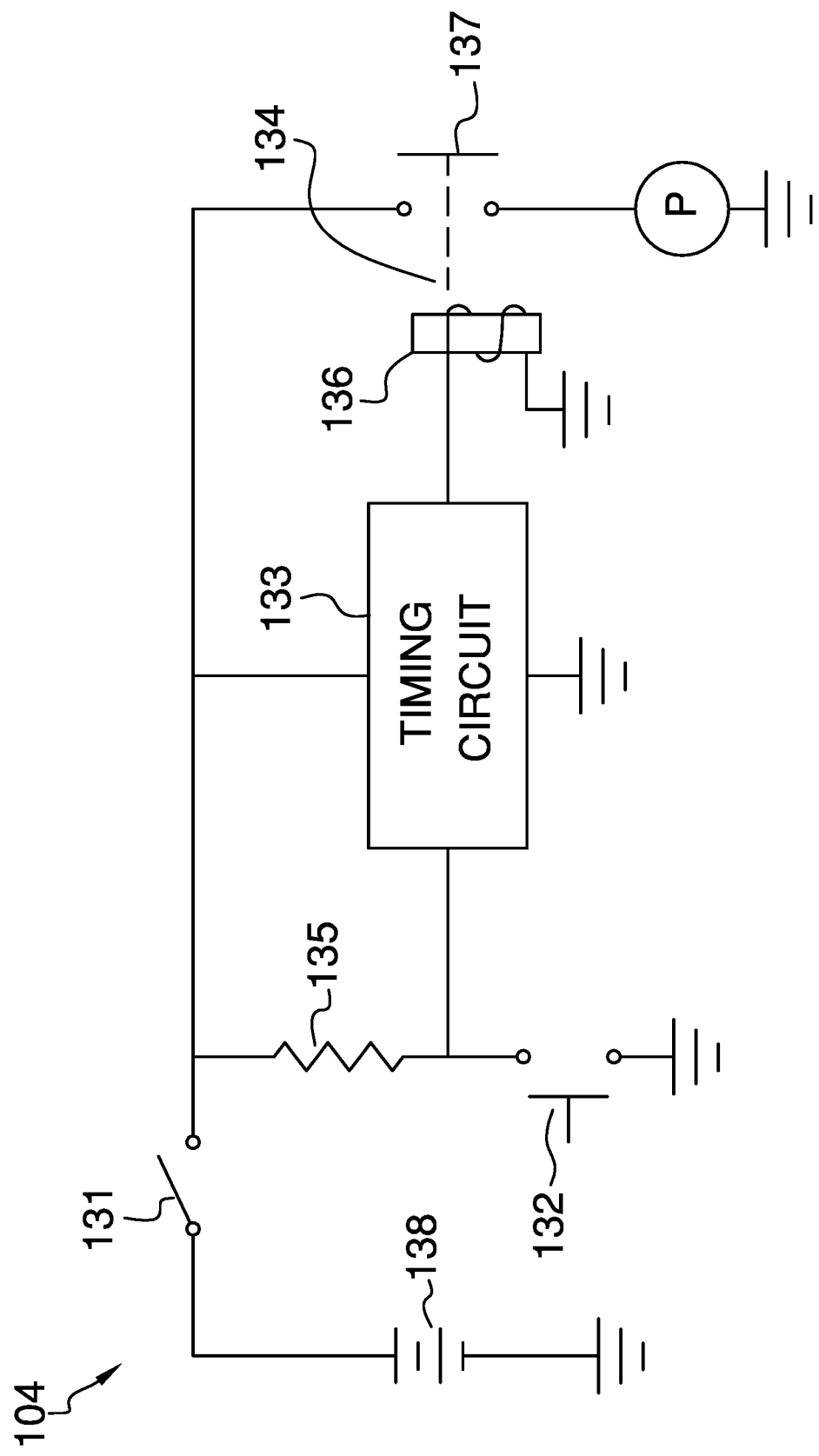
FIG. 4 is a block diagram of an embodiment of the disclosure.

Detailed reference will now be made to one or more potential embodiments of the disclosure, which are illustrated in FIGS. 1 through 4.

The mucus-removing device 100 (hereinafter invention) is adapted for use with a patient 161. The patient 161 is further defined with a tracheostomy tube 162. The patient 161 is defined elsewhere in this disclosure. The tracheostomy tube 162 is defined elsewhere in this disclosure.

The invention 100 is configured for use with the tracheostomy tube 162. The invention 100 generates a vacuum at the tracheostomy tube 162 such that mucus 181 is withdrawn from the pulmonary system through the tracheostomy tube 162 and into the invention 100. The invention 100 generates the vacuum at the tracheostomy for a fixed period of time. The periodic nature of the generation of the vacuum allows the patient 161 to breathe comfortably during the mucus 181 removal process. The invention 100 comprises a pump 101, a hose 102, a tracheostomy tube 162 connector 103, and a control system 104. The hose 102 attaches the pump 101 to the tracheostomy tube 162 connector 103. The tracheostomy tube 162 connector 103 attaches the invention 100 to the tracheostomy tube 162 of the patient 161.

The control system 104 regulates the operation of the pump 101. The pump 101 is a mechanical device. The pump 101 creates a pressure differential through the hose 102 that generates a vacuum that draws mucus 181 through the tracheostomy tube 162 into the hose 102. The pressure differential generated by the pump 101 further draws the mucus 181 through the hose 102 such that the pressure differential is maintained through the mucus 181 removal process. The pump 101 further comprises a pump fitting 141. The pump fitting 141 is a commercially available fitting that receives the first fitting 111 of the hose 102 to form a gas impermeable seal between the hose 102 and the pump 101.

The hose 102 is a flexible tube. The hose 102 transports the removed mucus 181 from the tracheostomy tube 162 to the pump 101. The hose 102 further comprises a first fitting 111 and a second fitting 112. The first fitting 111 is a commercially available fitting that inserts into the pump fitting 141 to form a gas impermeable seal between the hose 102 and the pump 101. The second fitting 112 is a commercially available fitting that inserts into the third port 173 of the tracheostomy tube 162 connector 103 to form a gas impermeable seal between the hose 102 and the tracheostomy tube 162 connector 103.

The tracheostomy tube 162 connector 103 is an apparatus that attaches to the hose 102. The tracheostomy tube 162 connector 103 attaches the hose 102 to the tracheostomy tube 162 such that the removed mucus 181 travels from the tracheostomy tube 162 into the hose 102 through the tracheostomy tube 162 connector 103. The tracheostomy tube 162 connector 103 is formed in the shape of a tee connector 121. The tracheostomy tube 162 connector 103 further comprises a tee connector 121, a capped end 122, a third fitting 123, and a fourth fitting 124. The tee connector 121 is further defined with a first port 171, a second port 172, and a third port 173.

The first port 171 is a cylindrical port that attaches to the tracheostomy tube 162. The second port 172 is a cylindrical port that forms the capped end 122 of the tracheostomy tube 162 connector 103. The center axes of the first port 171 and the second port 172 are aligned. The second port 172 is formed as a capped tube. The third port 173 is a cylindrical port that attaches to the hose 102. The center axis of the third port 173 is perpendicular to the center axes of the first port 171 and the second port 172.

The tee connector 121 is a hollow three port structure. The tee connector 121 is a well-known and documented pipe configuration that has the shape of the letter "T". The tee connector 121 receives the flow of gas and mucus 181 from the tracheostomy tube 162 and transports the flow of gas and mucus 181 to the hose 102.

The capped end 122 is formed as the second port 172 of the tee connector 121. The capped end 122 is a port the forms a fluidic connection between the hollow interior of the tee connector 121 and the atmosphere. The capped end 122 has a removable lid.

During the operation of the pump 101, the capped end 122 is kept in a closed position such that the pump 101 draws the flow of gas and mucus 181 into the hose 102. When the pump 101 is not in operation, the capped end 122 is manually opened such that the patient 161 can draw air from the atmosphere into the tracheostomy tube 162 connector 103 for breathing. The use of the capped end 122 is required when a tracheal tube is configured to prevent air flow from the lungs to the mouth of the patient 161. The use of the capped end 122 is suggested in other scenarios.

The third fitting 123 is a commercially available fitting that receives the second fitting 112 of the hose 102 to physically form the gas impermeable seal. The third fitting 123 is formed in the third port 173 of the tee connector 121. The fourth fitting 124 is a commercially available fitting that receives the tracheostomy tube 162 of the patient 161 to physically form a gas impermeable seal between the first port 171 of the tee connector 121 and the tracheostomy tube 162. The fourth fitting 124 is formed in the first port 171 of the tee connector 121.

The control system 104 is an electrical circuit. The control system 104 controls and regulates the operation of the pump 101. Specifically, the control system 104 initiates the operation of the pump 101. The control system 104 terminates the operation of the pump 101 after a predetermined interval of time. By limiting the period of operation of the pump 101, the control system 104 reduces the anxiety caused to the patient 161 by the mucus 181 removal process by allowing the patient 161 to breathe when the pump 101 is not in operation. The control system 104 comprises a master switch 131, an initiating switch 132, a timing circuit 133, a relay 134, a pull-up resistor 135, and an external power source 136. The relay 134 further comprises a relay coil 136 and a relay switch 137.

The master switch 131 is a commercially available maintained switch this is electrically connected in series between the external power source 136 and the balance of the control system 104. The master switch 131 forms the power switch of the invention 100. The initiating switch 132 is a commercially available momentary switch. The initiating switch 132 presents a voltage to the timing circuit 133. When the initiating switch 132 is actuated, the timing circuit 133 detects a change in voltage across the initiating switch 132, the timing circuit 133 initiates the operation of the timing circuit 133.

The timing circuit 133 is an electrical circuit. Once initiated by the initiating switch 132, the timing circuit 133 energizes the relay 134 for the predetermined interval of time. After the predetermined interval of time, the timing circuit 133 deenergizes the relay 134.

The relay 134 is an electrically controlled switching element. The relay 134 controls the flow of electricity from the master switch 131 to the pump 101 such that the relay 134 controls the operation of the pump 101 under the supervision of the timing circuit 133.

The relay coil 136 is a solenoid that is used to actuate the relay switch 137. The relay switch 137 is a normally open electrical switch that electrically connects in series between the master switch 131 and the pump 101. The relay switch 137" physically controls the flow of electricity into the motor of the pump 101.

The pull-up resistor 135 is a resistor placed in series between the master switch 131 and the initiating switch 132. The pull-up resistor 135 controls the flow of electricity through the initiating switch 132.

The external power source 138 is an externally provides source of electrical energy that is used to power the pump 101 and the control system 104.

The following definitions were used in this disclosure:

90 Degree Elbow: As used in this disclosure, a 90 degree elbow is a two aperture fitting that attaches a first pipe to a second pipe such that the center axis of the first pipe is perpendicular to the center axis of the second pipe.

Capped Tube: As used in this disclosure, a capped tube is a tube with one closed end and one open end.

Catheter: As used in this disclosure, a catheter is a flexible tube inserts into the body and through which fluids may be introduced into or removed from the body.

Closed Position: As used in this disclosure, a closed position refers to a movable barrier structure that is in an orientation that prevents passage through a port or an aperture. The closed position is often referred to as an object being "closed." Always use orientation.

External Power Source: As used in this disclosure, an external power source is a source of the energy that is externally provided to enable the operation of the present disclosure. Examples of external power sources include, but are not limited to, electrical power sources and compressed air sources.

Fitting: As used in this disclosure, a fitting is a component that is attached to a first object. The fitting is used to forming a fluidic connection between the first object and a second object.

Hose: As used in this disclosure, a hose is a flexible hollow cylindrical device used for transporting liquids and gases.

Lid: As used in this disclosure, a lid is a removable cover that is placed over an opening of a hollow structure to enclose the hollow structure.

Maintained Switch: A used in this disclosure, a maintained switch is a switch that maintains the position that was set in the most recent switch actuation. A maintained switch works in an opposite manner to a momentary switch.

Momentary Switch: As used in this disclosure, a momentary switch is a biased switch in the sense that the momentary switch has a baseline position that only changes when the momentary switch is actuated (for example when a pushbutton switch is pushed). The momentary switch then returns to the baseline position once the actuation is completed. This baseline position is called the "normal" position. For example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

Patient: As used in this disclosure, a patient is a person who is designated to receive a medical treatment, therapy or service. The term patient may be extended to an animal when used within the context of the animal receiving veterinary treatment or services Pull-Up Resistor: As used in this disclosure, a pull-up resistor is an electrical resistor used to: 1) limit the current flow through a switching device; and, 2) to control the voltage level presented across a load resistor or a pull-down resistor.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Open Position: As used in this disclosure, an open position refers to a movable barrier structure that is in an orientation that allows passage through a port or an aperture. The open position is often referred to as an object being "open."

Orientation: As used in this disclosure, orientation refers to the positioning of a first object relative to: 1) a second object; or, 2) a fixed position, location, or direction.

Relay: As used in this disclosure, a relay is an automatic electromagnetic or electromechanical device that reacts to changes in voltage or current by opening or closing a switch in an electric circuit. Relays further defined with a coil and a switch. Applying a voltage to the coil, usually referred to as energizing the coil, will cause the coil to change the position of the switch.

Resistor: As used in this disclosure, a resistor is a well-known and commonly available electrical device that inhibits the flow of electricity through an electric circuit. Within an electric circuit processing alternating currents, the resistor will not affect the phase of the alternating current. A current flowing through a resistor will create a voltage across the terminals of the resistor.

Stoma: As used in this disclosure, a stoma is an aperture that is formed through a membrane or surface to allow for the passage of material through the membrane or surface. In certain medical situation, the use of the term stoma will further imply that the aperture leads to a hollow organ such as the stomach.

Solenoid: As used in this disclosure, a solenoid is a cylindrical coil of electrical wire that generates a magnetic field that can be used to mechanically move a shaft made of a magnetic core.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Tee Connector: As used in this disclosure, a T Connector is a three aperture fitting that is designed to connect a first pipe, a second pipe and a third pipe such that: 1) the center axis of the first pipe is aligned with the center axis of the second pipe; 2) the center axis of the third pipe is perpendicular to the aligned center axes of the first pipe and the second pipe; and, 3) the center axes of the first pipe, the second pipe, and the third pipe intersect at a single point. The tee connector is a commercially available plumbing and PVC pipe fitting.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry. The "555" timing circuit is a well-known, documented, and commercially available timing circuit.

Tracheal Tube: As used in this disclosure, a tracheal tube is a catheter that inserts into the trachea to provide an open passage for the flow of air into the lungs.

Tracheostomy: As used in this disclosure, a tracheostomy is an opening cut in the neck of a patient through which a tracheal tube inserts.

Tracheostomy Tube: As used in this disclosure, a tracheostomy tube is a rigid tube that inserts in the stoma formed by a tracheostomy that prevents the stoma from prematurely closing.

Tube: As used in this disclosure, a tube is a hollow cylindrical device used for transporting liquids and gases. The line that connects the center of the first base of the cylinder to the center of the second base of the cylinder is referred to as the center axis of the tube or the centerline of the tube. In this disclosure, the terms inner diameter of a tube and outer diameter of a tube are used as they would be used by those skilled in the plumbing arts.

Vacuum: As used in this disclosure, vacuum is used to describe a first space that contains gas at a reduced gas pressure relative to the gas pressure of a second space. If the first space and the second space are connected together, this pressure differential will cause gas from the second space to move towards the first space until the pressure differential is eliminated.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A self-contained vacuum aspirator comprising
a pump, a hose, a tracheostomy tube connector, and a control system;
wherein the hose attaches the pump to the tracheostomy tube connector;
wherein the tracheostomy tube connector attaches the self-contained vacuum aspirator to a tracheostomy tube of a patient;
wherein the control system regulates the operation of the pump;
wherein the self-contained vacuum aspirator is adapted for use with a patient;
wherein the vacuum aspirator is configured to interface with a patient having a tracheostomy tube, a pulmonary system, and mucus;
wherein the self-contained vacuum aspirator is configured for use with a tracheostomy tube;
wherein the self-contained vacuum aspirator generates a vacuum at the tracheostomy tube such that mucus is withdrawn from the pulmonary system through the tracheostomy tube and into the self-contained vacuum aspirator;
wherein the self-contained vacuum aspirator generates the vacuum at the tracheostomy for a fixed period of time;
wherein the hose further comprises a first fitting and a second fitting;
wherein the first fitting attaches to an end of the hose;
wherein the second fitting attaches to an end of the hose that is distal from the first fitting;
wherein the pump further comprises a pump fitting;
wherein the pump fitting receives the first fitting of the hose to form a gas impermeable seal between the hose and the pump;
wherein the first fitting inserts into the pump fitting;
wherein the control system comprises a master switch, an initiating switch, a timing circuit, a relay, a pull-up resistor,
wherein the control system is configured for use with an external power source;
wherein the master switch, the initiating switch, the timing circuit, the relay, and the pull-up resistor are electrically interconnected;
wherein the master switch is a maintained switch;
wherein the master switch electrically connects in series between the external power source and the control system.

2. The self-contained vacuum aspirator according to claim 1
wherein the pump is a mechanical device;
wherein the pump creates a pressure differential through the hose;
wherein the pressure differential draws mucus through the tracheostomy tube into the hose;
wherein the pressure differential draws the mucus through the hose.

3. The self-contained vacuum aspirator according to claim 2 wherein the hose is a flexible tube;
wherein the hose transports the removed mucus from the tracheostomy tube to the pump.

4. The self-contained vacuum aspirator according to claim 3
wherein the tracheostomy tube connector attaches to the hose;
wherein the mucus removed by the pump travels from the tracheostomy tube into the hose through the tracheostomy tube connector.

5. The self-contained vacuum aspirator according to claim 4
wherein the control system is an electrical circuit;
wherein the control system controls and regulates the operation of the pump;
wherein the control system initiates the operation of the pump;
wherein the control system terminates the operation of the pump after a predetermined interval of time.

6. The self-contained vacuum aspirator according to claim 5 wherein the aspirator comprises a first cylindrical port; a second cylindrical port and; a third cylindrical port.

7. The self-contained vacuum aspirator according to claim 6
wherein the first port attaches to the tracheostomy tube;
wherein the second port forms a capped end of the tracheostomy tube connector;
wherein the third port attaches to the hose.

8. The self-contained vacuum aspirator according to claim 7
wherein a center axis of the first port and the second port are aligned;
wherein the center axis of the third port is perpendicular to the center axes of the first port and the second port.

9. The self-contained vacuum aspirator according to claim 8 wherein the second port is formed as a capped tube;
wherein a capped end is a port that forms a fluidic connection between a hollow interior of a tee connector and the atmosphere.

10. The self-contained vacuum aspirator according to claim 9
wherein the capped end comprises a removable lid;
wherein during the operation of the pump, the capped end is kept in a closed position;
wherein when the pump is not in operation, the capped end is open.

11. The self-contained vacuum aspirator according to claim 10 wherein the second fitting inserts into the third port of the tracheostomy tube connector to form a gas impermeable seal.

12. The self-contained vacuum aspirator according to claim 11 wherein the third fitting is formed in the third port of the tee connector.

13. The self-contained vacuum aspirator according to claim 12 wherein a fourth fitting receives the tracheostomy tube of the patient to physically form a gas impermeable seal between the tee connector and the tracheostomy tube;

wherein the fourth fitting is formed in the first port of the tee connector.

14. The self-contained vacuum aspirator according to claim 13 wherein the initiating switch is a momentary switch;

wherein the initiating switch presents a voltage to the timing circuit;

wherein the pull-up resistor is a resistor placed in series between the master switch and the initiating switch;

wherein the pull-up resistor controls the flow of electricity through the initiating switch.

15. The self-contained vacuum aspirator according to claim 14 wherein the timing circuit is an electrical circuit;

wherein the timing circuit detects a change in voltage across the initiating switch;

wherein the timing circuit energizes the relay for the predetermined interval of time.

16. The self-contained vacuum aspirator according to claim 15 wherein the relay is an electrically controlled switching element;

wherein the relay controls the flow of electricity from the master switch to the pump.

17. The self-contained vacuum aspirator according to claim 16 wherein the relay further comprises a relay coil and a relay switch;

wherein the relay coil is a solenoid used to actuate the relay switch;

wherein the relay switch is a normally open electrical switch that electrically connects in series between the master switch and the pump;

wherein the relay switch physically controls the flow of electricity into a motor of the pump.

* * * * *